(12) United States Patent
Yamamori et al.

(10) Patent No.: US 6,267,928 B1
(45) Date of Patent: Jul. 31, 2001

(54) CAPNOMETER

(75) Inventors: Shinji Yamamori; Hidehiro Hosaka; Kohei Ono; Masami Ito; Masayuki Inoue; Masaki Sugiura; Noriaki Todokoro; Yoshinobu Nakae, all of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/112,324

(22) Filed: Jul. 9, 1998

Related U.S. Application Data (63) Continuation-in-part of application No. 08/605,843, filed on Feb. 26, 1996, now abandoned.

(30) Foreign Application Priority Data

| Feb. 24, 1995 | (JP) | 7-036699 |
| Feb. 24, 1995 | (JP) | 7-037239 |
| Feb. 24, 1995 | (JP) | 7-037361 |
| Feb. 24, 1995 | (JP) | 7-037411 |
| Feb. 24, 1999 | (JP) | 7-037324 |

(51) Int. Cl.$^7$ .................................................. G01N 33/497
(52) U.S. Cl. ........................................... 422/84; 436/133
(58) Field of Search ..................... 422/83, 84; 436/133, 436/134; 128/719; 600/532

(56) References Cited

U.S. PATENT DOCUMENTS

| 4,067,320 | 1/1978 | Olsson et al. | |
| 4,648,396 | 3/1987 | Raemer. | |
| 4,653,498 | 3/1987 | New, Jr. et al. | 128/633 |
| 5,281,817 | 1/1994 | Yelderman et al. | 250/343 |
| 5,386,833 | 2/1995 | Uhen | 128/719 |
| 5,401,966 | 3/1995 | Gray et al. | 250/343 |
| 5,616,823 | * 4/1997 | Lattimore | 73/632 |
| 5,728,585 | 3/1998 | Yamamori et al. | 436/133 |
| 5,743,259 | * 4/1998 | Kruse et al. | 128/632 |
| 5,836,300 | * 11/1998 | Mault | 128/204.23 |
| 5,954,050 | * 9/1999 | Christopher | 128/204.23 |

FOREIGN PATENT DOCUMENTS

| 0 512 535 | 11/1992 | (EP). |
| 51-136474 | 11/1976 | (JP). |
| 53-53184 | 5/1978 | (JP). |
| 59-160446 | 9/1984 | (JP). |
| WO 91 03204 | 3/1991 | (WO). |

\* cited by examiner

*Primary Examiner*—Jeffrey Snay
(74) *Attorney, Agent, or Firm*—Sughrue, Mion, Zinn, Macpeak & Seas, PLLC (57) ABSTRACT

A method and apparatus for applying infrared radiation to a respiratory gas and detects a signal associated with the quantity of transmitted radiation for measuring the concentration of $CO_2$ in the respiratory gas. The capnometer detects a maximum value of the detection signal from the thermal detector during the present inspiration phase, stores the detected maximum value in RAM, performs the first approximation, Kalman filtering or some other suitable method to compute a corrected value that is valid for the time being until a maximum value is detected in the next inspiration phase, and determines a density signal by calculating the difference between the corrected value and the detection signal.

18 Claims, 7 Drawing Sheets

CAPNOMETER

This is a continuaiton-in-part of application Ser. No. 08/605,843, filed Feb. 26, 1996, now abandoned.

BACKGROUND OF THE INVENTION

1. Field of the Invention

The present invention relates to a capnometer for measuring the concentration of carbon dioxide in expired gases.

2. Related Art

Infrared measurements of carbon dioxide in expired gases are commonly performed with radiation detectors that sense the transmission of radiation associated with the absorption by the carbon dioxide during expiration. The output voltage of the detector is subject to drift for various reasons including the variation in the intensity of radiation from the source and the change in the quantity of radiation due to the contamination of the windows in the sensing part. An apparatus adapted to compensate for such drift is known in the art (see Examined Japanese Patent Publication No. 44614/1985; U.S. Pat. No. 4,067,320).

A problem with this capnometer equipped with the prior art drift compensator in a radiation detector is that the detector uses the rather expensive PbSe. This material features fast response but the device temperature will increase upon continued exposure to an infrared radiation and the decreasing resistance will increase the drift. To avoid this problem, the radiation from the source has to be repeatedly chopped at a frequency, say, 25 ms, interval higher than the respiration frequency. To meet this need, a radiation interrupter and a drive mechanism such as a motor that drives its rotation have been used to detect the quantity of radiation passing through the respiratory gas. However, this has limited the efforts to reduce the overall size of the system and its power consumption while assuring ruggedness. In addition, the prior art system has had the disadvantage of being costly.

Thus, the Applicant developed a capnometer which is capable of compensating for a sensitivity drift of the detector included in the detecting signal and a sensitivity drift, without employing any mechanism for cyclically chopping the infrared light necessary for the PbSe radiation detector (U.S. patent application Ser. No. 08/606,845, now U.S. Pat. No. 5,825,560).

According to the Applicant's proposed technique, the density signal is calculated from the difference between the maximum value of the detection signal during the inspiration phase and the detected signal corresponding to the expiration phase. A reference value is calculated by determining the difference between the maximum value in the inspiration phase and the offset voltage value. However, the Applicant's proposed technique is deficient for the following reasons.

Figure 7:
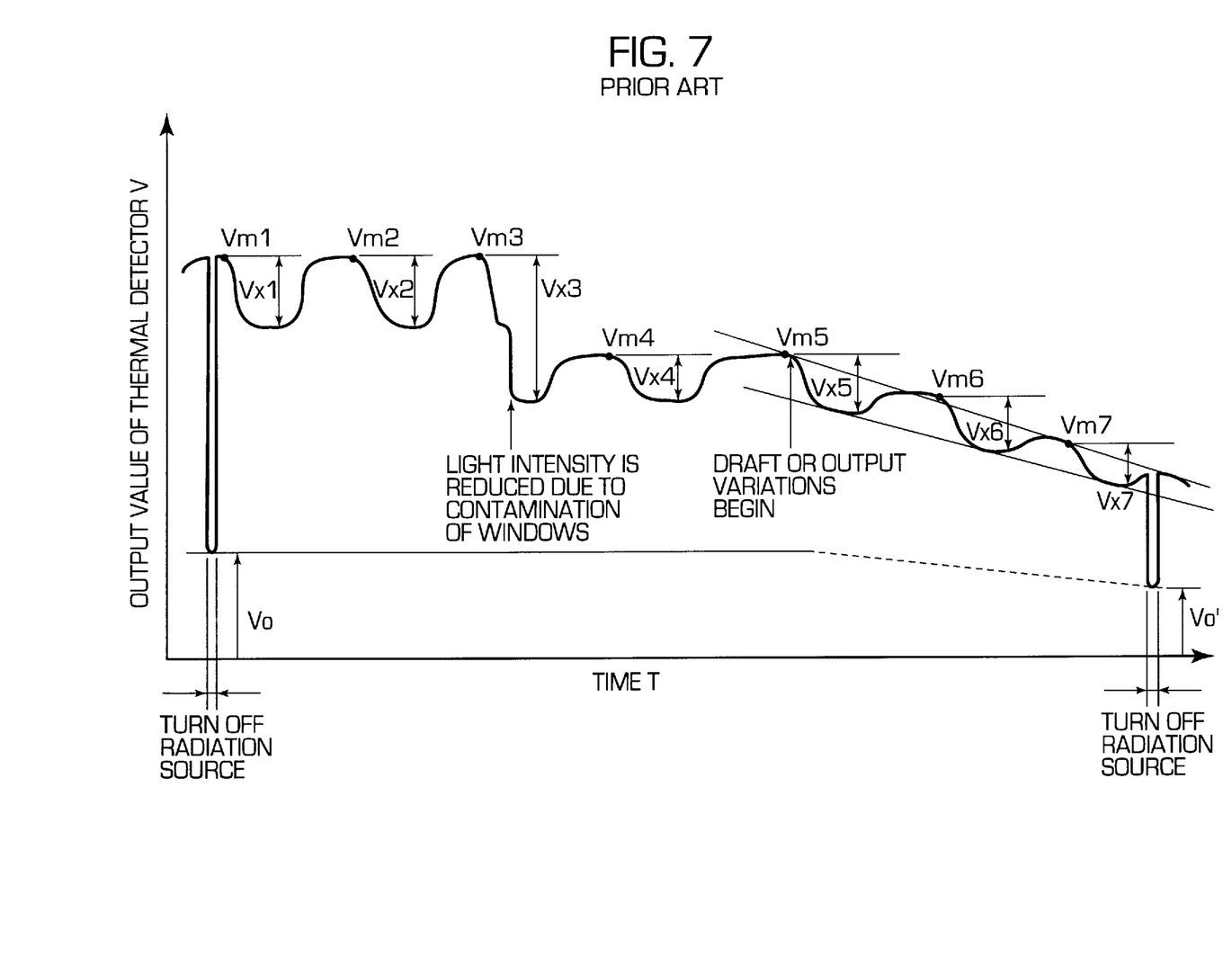
FIG. 7 is a diagram illustrating the operating theory of the prior art drift compensation for the detected signal from the thermal detector.

Suppose that once the offset voltage value is detected when the radiation source is turned off momentarily and stored, the reference value is not replaced until the next offset voltage value is detected. This condition results in the following problem for example, as shown in FIG. 7. (1) when light intensity is reduced due to contamination of windows, the difference between the maximum value and the detected signal may contain reduced quantity of detected signal due to the light intensity decrement. So, the measured value may be larger than the actual value as shown by V×3 in FIG. 7. (2) As sensitivity decreases, the amplitude of the detected signal caused by changes of $CO_2$ concentration in the expiration phase is decreased gradually. Since the reference value calculated before the light intensity is reduced is maintained and not replaced until the next maximum value is detected during the next inspiration phase, employing the ratio of such reference value and the density value results in obtaining a measured concentration value which is smaller than actual value and is incorrect as shown by V×4 in FIG. 7. (3) In the process where the detected signal is decreasing due to thermal drift or sensitivity variations, as mentioned above, the amplitude of detected signal caused by changes of $CO_2$ concentration in expiration phase is decreased gradually. This phenomenon occurs due to the tendency of the measured value to become smaller than the actual value. On the other hand, since the maximum values detected in inspiration phases decrease, the difference between the maximum value detected in the inspiration phase and the detected signal detected in the expiration phase reflect the tendency that the measured value becomes larger than the actual value. Therefore, changes of obtained measured values depend on the degree of drift or sensitivity variations which may operate simultaneously (See V×5~V×7 in FIG. 7).

Suppose that replacement of the reference value is performed every respiration by employing the maximum value at each inspiration phase. Under such conditions, the problems noted above may not be resolved as long as the offset voltage value per se drifts.

SUMMARY OF THE INVENTION

It is an object of the present invention to provide a capnometer having a thermopile that is adapted to compensate for both drift and output variations.

In the conventional devices with thermopiles, as mentioned above, the density signal is calculated using the difference between the maximum value obtained during the inspiration phase and the detected signal. According to the present invention, the density signal is determined by calculating the difference between a corrected value and the detected signal.

Further, in the conventional devices, a reference signal is calculated using the difference between the maximum value detected during the inspiration phase and the offset voltage value. According to the present invention, the reference signal is to determined by calculating the difference between the corrected value and the offset voltage value.

In the present invention, for drift compensation, the radiation is turned off momentarily and then turned on periodically and repeatedly. When the radiation source is turned off, a minimum output value is detected as the offset voltage value of the thermopile and stored. Since the offset voltage value contains the drift caused by the structure of thermopile per se due to rapid temperature changes, calculation of the difference between the output value of thermal detector and the offset voltage value which is detected every predetermined period enables compensation of drift caused by changes of temperature.

DETAILED DESCRIPTION OF THE PREFERRED EMBODIMENTS

Before going into details of the embodiments of the present invention, we first describe the operating theory of the invention. The invention uses a thermopile as a thermal detector for sensing the intensity of an infrared radiation as it varies with the concentration of $CO_2$ in an expired gas. Thermopiles are subject to a smaller amount of drift than the conventional PbSe and they are less expensive. On the other hand, thermopiles have unique properties and must be used in compliance with such characteristics. First of all, the light source chopping operation obtaining a response speed slower than 25 ms are said to be necessary for accomplishing precise sampling with capnometers; however, thermopiles are so slow in response (50~200 ms) that it is difficult to meet this requirement for response.

Another problem with the capnometer using a thermopile is that the detection signal can potentially contain drift components due to various factors such as the change in the quantity of infrared rays from the radiation source, the clouding or contamination of windows in the expired gas sensing portion and the structure of the thermopile per se. The drift compensation due to the structure of the thermopile must be compensated since it occurs on account of the change in the temperature of the environment in which the capnometer is used. Stated more specifically, the thermopile has many couples of hot and cold junctions and due to the time constant mismatch between the two junctions, a drift will appear in the detected signal. The hot junction having a small heat capacity will respond rapidly to an abrupt change in the ambient temperature; however, the cold junctions which make thermal contact with the vessel or heat sink have a large heat capacity and do not respond as fast as the hot junction. As a result, the detected signal which is delivered in accordance with the temperature difference between the hot and cold junctions will contain an undesired drift component until the cold junction achieves thermal equilibrium with the ambient temperature. However, changes of this kind of drift are slower than that of $CO_2$ concentration.

The clouding and contamination of the windows also reduces the transmission of infrared radiation, thereby changing the output of the thermopile, namely, an amplitude of the output. This affects the $CO_2$ concentration, making it impossible to perform consistent $CO_2$ measurement.

A specific procedure for sensitivity correction comprises sensing a maximum value of the detection signal from the thermopile in each inspiration phase, storing the sensed maximum value, calculating the corrected value until next maximum value in inspiration phase is detected, detecting an output value in each subsequent expiration phase and calculating the difference between the corrected value and the output value for the subsequent expiration phase so as to determine a density signal.

Then, the ratio of the difference between the calculated corrected value and the stored offset voltage value (output corresponding to the light intensity when the $CO_2$ concentration is zero) to the difference between the corrected value and the output value in the expiration phase (output corresponding to the light intensity absorbed by $CO_2$ gas in expired gas) is determined, and is used to calculate the correct $CO_2$ concentration using Lambert-Beer's law as follows:

$$\frac{Veo - Vfe}{Veo} = \exp(-\delta CL) \tag{1}$$

where C:$CO_2$ concentration:

δ: absorbance coefficient;

L: light path of infrared beam passing through respiratory gas. (a distance between windows W1 and W2 of an air duct in the embodiment)

Figure 1:
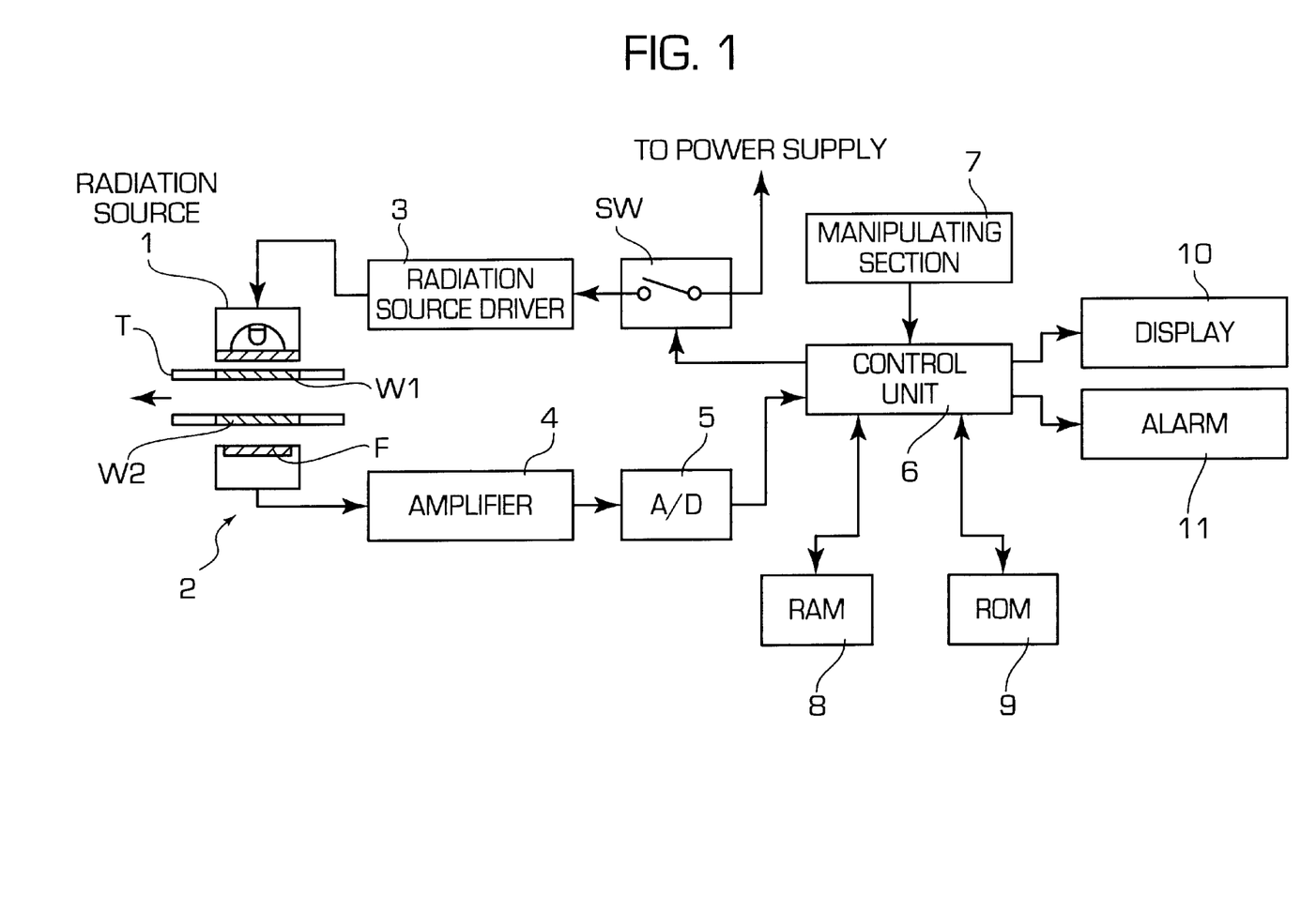
FIG. 1 is a block diagram showing the composition of the capnometer of the invention.

Veo: output corresponding to the light intensity when the $CO_2$ concentration is zero Vfe: output corresponding to the light intensity absorbed by $CO_2$ gas in expired gas Referring now to FIG. 1, symbol T designates an air way adapter through which both the expired and inspired gas will pass. Windows W1 and W2, each made of a transparent material such as a plastic sheet, are formed in opposed areas of the air way adapter. One end portion of the air way adapter T (which is on the left of FIG. 1) serves as a mouthpiece which is to be inserted into the mouth of the patient and the other end portion (which is on the right of FIG. 1) is open to the atmosphere. Both windows W1 and W2 are protected against clouding such as with the water vapor in the expired gas. An infrared radiation source 1 such as an infrared lamp is provided just above the window W1 such that infrared radiation is applied through the window W1. A thermal detector 2 in the form of the above-described thermopile is provided just below the window W2 such that the infrared radiation supplied from the source 1 through the windows W1 and W2 is detected. A filter F is located in the light-receiving surface of the thermal detector 2 and it selectively passes those rays which have such a wavelength (about 4.3 $\mu$m) that they are absorbed by carbon dioxide in the expired gas.

Shown by 3 is a radiation source drive unit that is typically composed of a constant-current circuit and which allows the source 1 to emit an infrared radiation of a constant intensity. The drive unit 3 is connected to a switch SW which is operated by a control unit (to be described later) to turn the radiation source 1 on and off as required. Switch SW is typically composed of an electronic switch such as a transistor and normally on. Shown by 4 is an amplifier for amplifying the detection voltage of the thermal detector 2; 5 is an analog-digital converter for converting the output of amplifier 4 to a digital signal. Control unit 6 is typically composed of a CPU and controls the overall system in accordance with a $CO_2$ measuring control program stored in ROM 9 which will be described later.

Shown by 7 is a manipulating section typically composed of a plurality of buttons which are to be touched for various purposes such as turning the radiation source 1 on and off in a trial operation and providing settings of the necessary data.

Shown by 8 is a RAM that temporarily stores and holds various data including the parameter settings and the measured $CO_2$ concentrations; 9 is a ROM which contains a control program for performing automatic $CO_2$ concentration measurements by compensating for the drift in the voltage output from the thermal detector 2 in accordance with the above-described operating theory of the present invention.

Figure 6:
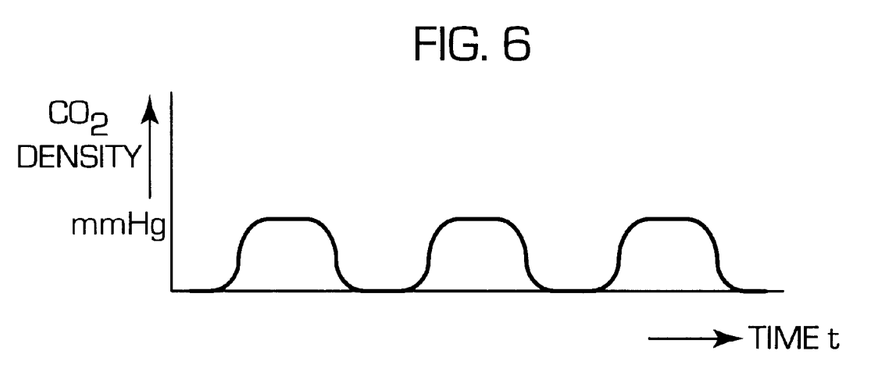
FIG. 6 is a timing chart showing the waveforms obtained by measuring the $CO_2$ concentration in the embodiments.

The determined concentration is displayed on the display unit 10. If the display unit is a bar graph, lengths of bars will vary in accordance with the $CO_2$ concentration changes as shown in FIG. 6.

Figure 2:
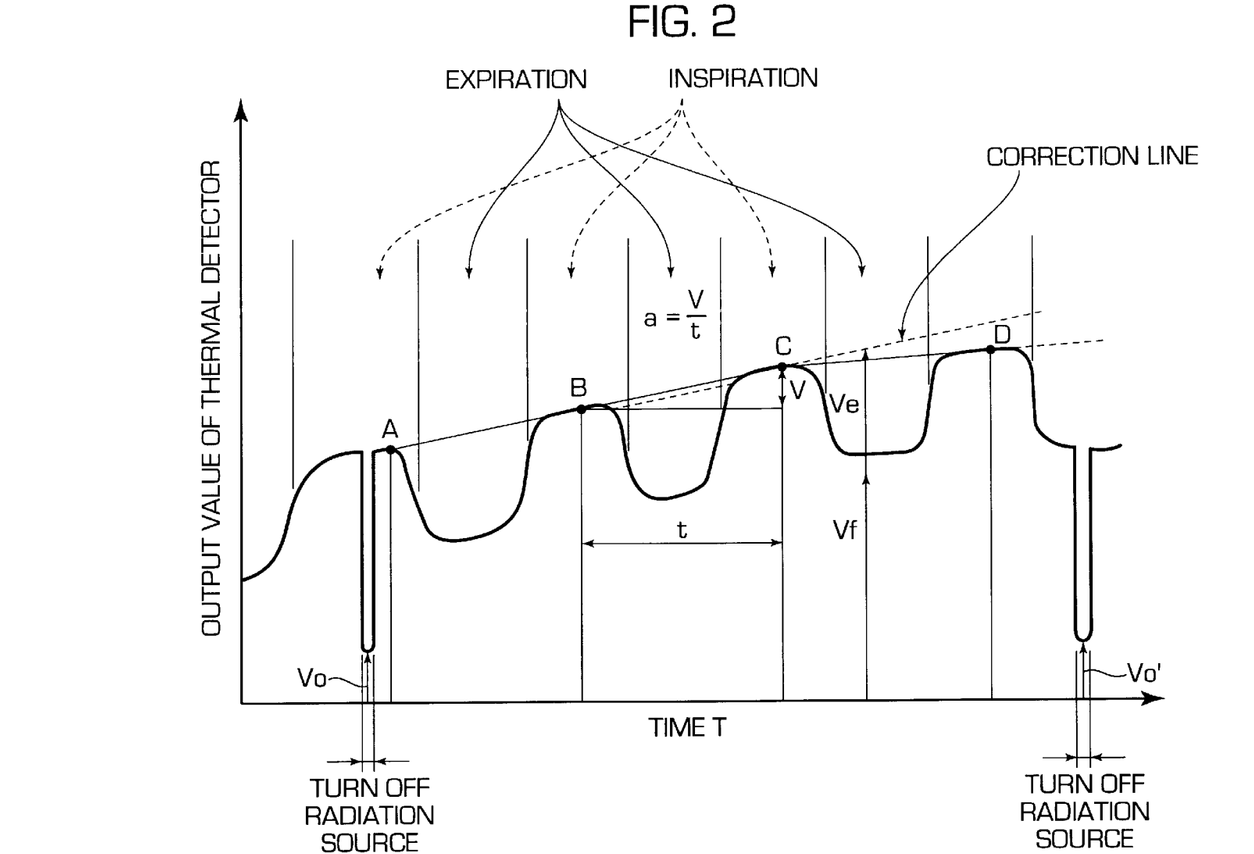
FIG. 2 is a diagram illustrating the operating theory of the invention by means of correction lines for the detected signal from the thermal detector.

FIG. 2 is a timing chart showing the waveforms obtained in compensation for the drift in the output of the thermal detector using correction lines in accordance with a first embodiment of the invention. The radiation source 1 is turned off momentarily and then turned on by controlling SW, and when the radiation source is turned off, a minimum output value Vo is detected as the offset voltage value of thermopile and stored. The changes of the offset voltage values indicates the tendency of thermal drift. Symbols A–D represent the points at which maxima are sensed for the detection signal from the thermopile during successive inspiration phases. The compensating procedure typically goes like this: if B is supposed to be the point at which a maximum value is sensed by the thermopile during the present inspiration phase, point A at which a maximum value was sensed by the thermopile during the preceding inspiration phase is connected to point B by a straight (solid) line and the line is extended up to point C where a maximum value is sensed during the subsequent inspiration phase (the extended line is dashed and referred to as a "correction line"); similarly, if C is supposed to be the point at which a maximum value is sensed by the thermopile during the present inspiration phase, point B at which a maximum value was sensed during the preceding inspiration phase is connected to point C by a straight line and the line is extended up to point D where a maximum value is sensed during the subsequent inspiration phase (the extended line is also dashed and referred to as "correction line"). Output values from the thermopile are sensed for the expiration phases subsequent to the respective points of maxima sensing and subtracted from the associated correction lines to determine density signals. The density signals and the offset voltage value are used as a basis for computing the $CO_2$ concentration.

The straight line connecting two points of maxima detection in successive inspiration phases may be provided by a stored equation for straight line v= at, where v is the difference between maxima at the two points, t is the time difference between the two points, and a is the slope of the line. Referring to FIG. 2, the straight (solid) line connecting two points, B and C, may be determined on the basis of the detected maxima, which are stored and processed by the equation v= at, where the horizontal distance between the maxima being taken as the time difference t between points B and C, the vertical distance between the maxima being taken as v, and the ratio of v to t (v/t) being taken as the slope a.

According to this embodiment, the degree of discontinuities applied to the detection signal is reduced as compared with previous devices which determine density signals based on the difference between the maxima values during inspiration when the drift appears in a one way direction (in this embodiment, upper direction) such as points B–C–D.

Figure 3:
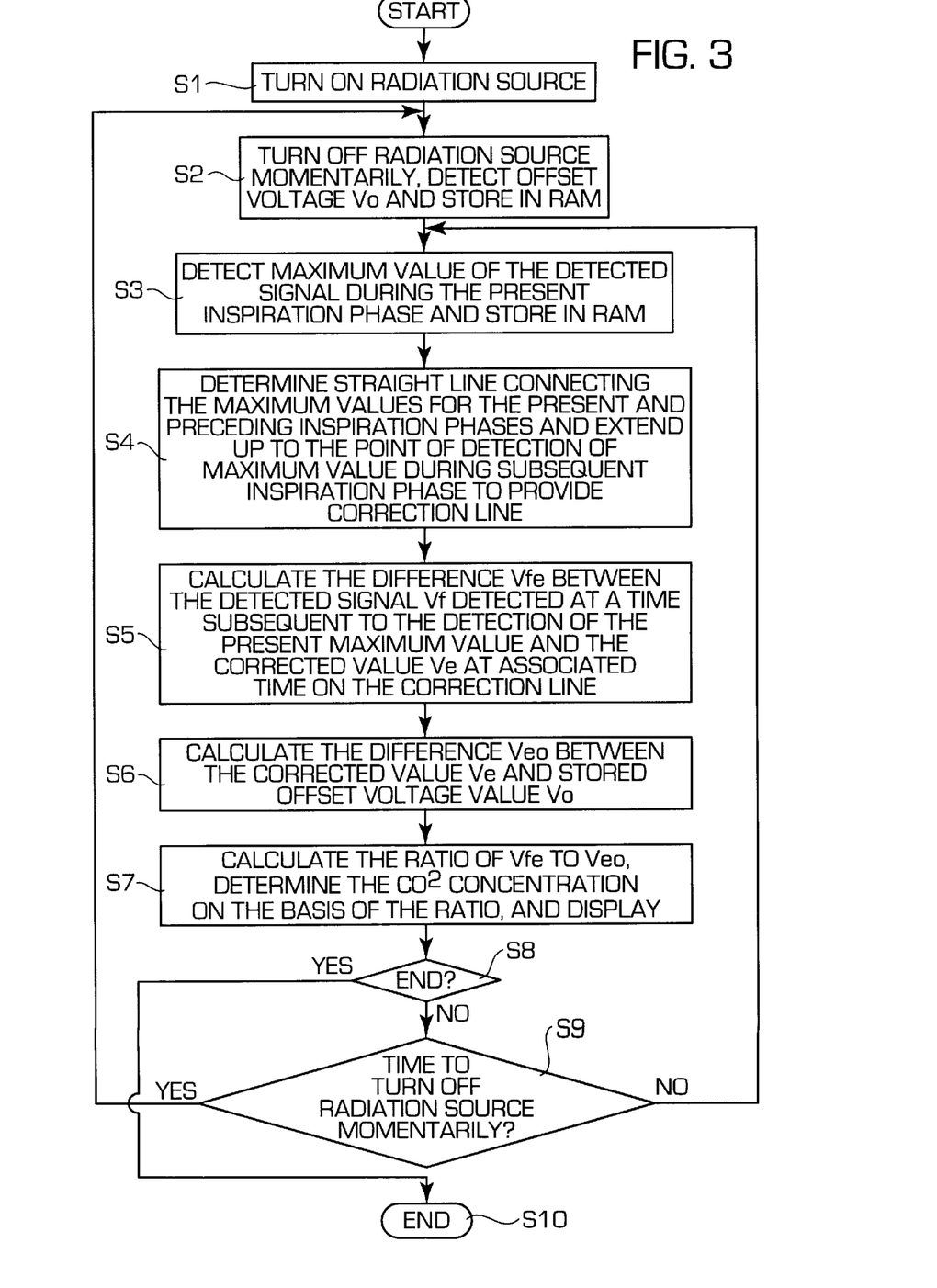
FIG. 3 is a flowchart describing the sequence of processing steps in the embodiment shown in FIG. 2.

The operation of the capnometer according to the present invention will now be described with reference to the flowchart shown in FIG. 3. At the commencement of measurement, the power switch (not shown) turns on the radiation source 1 (Step S1) Thereafter, the patient is allowed to breathe so that his respiratory gas goes into and comes out of the air way adapter T via the mouthpiece in his mouth.

The transmission of the radiation, which varies with the change in the $CO_2$ concentration of the respiratory gas, is received by the thermal detector 2 in such a way that the point at which the detector 2 delivers an increased output is recognized as an inspiration.

The radiation source 1 is turned off momentarily and then turned on by controlling switch SW, and when the radiation source is turned off, a minimum output value Vo is detected as the offset voltage value of thermopile and stored (Step S2).

During the inspiration phase, a maximum value corresponding to $CO_2$ concentration of zero is picked up from the detection signal from the thermal 2 and stored in RAM 8 (Step S3). The desired maximum value can be identified by performing a suitable processing on the detection signal from the thermal detector 2, for example, by calculating the differential for successive data on the time base.

The maximum output value for the present inspiration phase that has been picked up by the thermal detector 2 in step S3 is connected by a straight line to the maximum value for the preceding inspiration phase on the basis of the foregoing operating theory behind the described embodiment of the invention and the connecting line is extended as a correction line up to the point where a maximum value for the subsequent inspiration phase is detected (Step S4).

Then, since a detected signal Vf from the thermal detector 2 is decreasing subsequent to the detection of the present maximum value, the detected signal is recognized as representing an expiration phase. The difference Vfe between the detected signal Vf and a corrected value Ve, which is a point located on the correction line determined at the time when the detected signal Vf is detected, is determined, as shown in FIG. 2. Further, the difference Veo between the corrected value Ve and the stored offset voltage value Vo is calculated (Step S6), and the $CO_2$ concentration value is determined on the basis of the ratio of the difference values of Vfe to Veo (Step S7).

As long as the measurement is not terminated (Step S8), the offset voltage value Vo is detected at the time when the switch SW is turned off by switch control, stored and replaced (Step S9), and Step S2 through Step S8 are repeatedly performed. On the other hand, until the switch SW is turned off by the switch control, Step S3 through Step S9 are continuously performed to measure the $CO_2$ concentration at each respiration.

The control unit 6 determines the $CO_2$ concentration on the basis of the ratio of Vfe to Veo, and obtains changes in $CO_2$ concentration as shown in FIG. 6. The determined concentration is displayed on the display unit 10. If the display unit 10 is bar graph, varying lengths of bars will appear in accordance with the $CO_2$ concentration changes as shown in FIG. 6.

Thus, in this embodiment of the invention, the correction value line is extended up to a point of detection of a maximum value for each subsequent inspiration phase and used to determine the concentration. Even if the detected signal from the thermal detector contains a large drift component that produces a discontinuity between two successive expiration phases for the determination of signal, satisfactory drift compensation can be accomplished by the method of this embodiment.

A second embodiment of the invention will now be described with reference to the case where drift compensation is performed by Kalman filtering which is known as one of the computer techniques used to give a best estimate for a given system. Kalman filtering is also known to be capable of processing on a real-time basis and, hence, providing good accommodation of the latest data.

Figure 4:
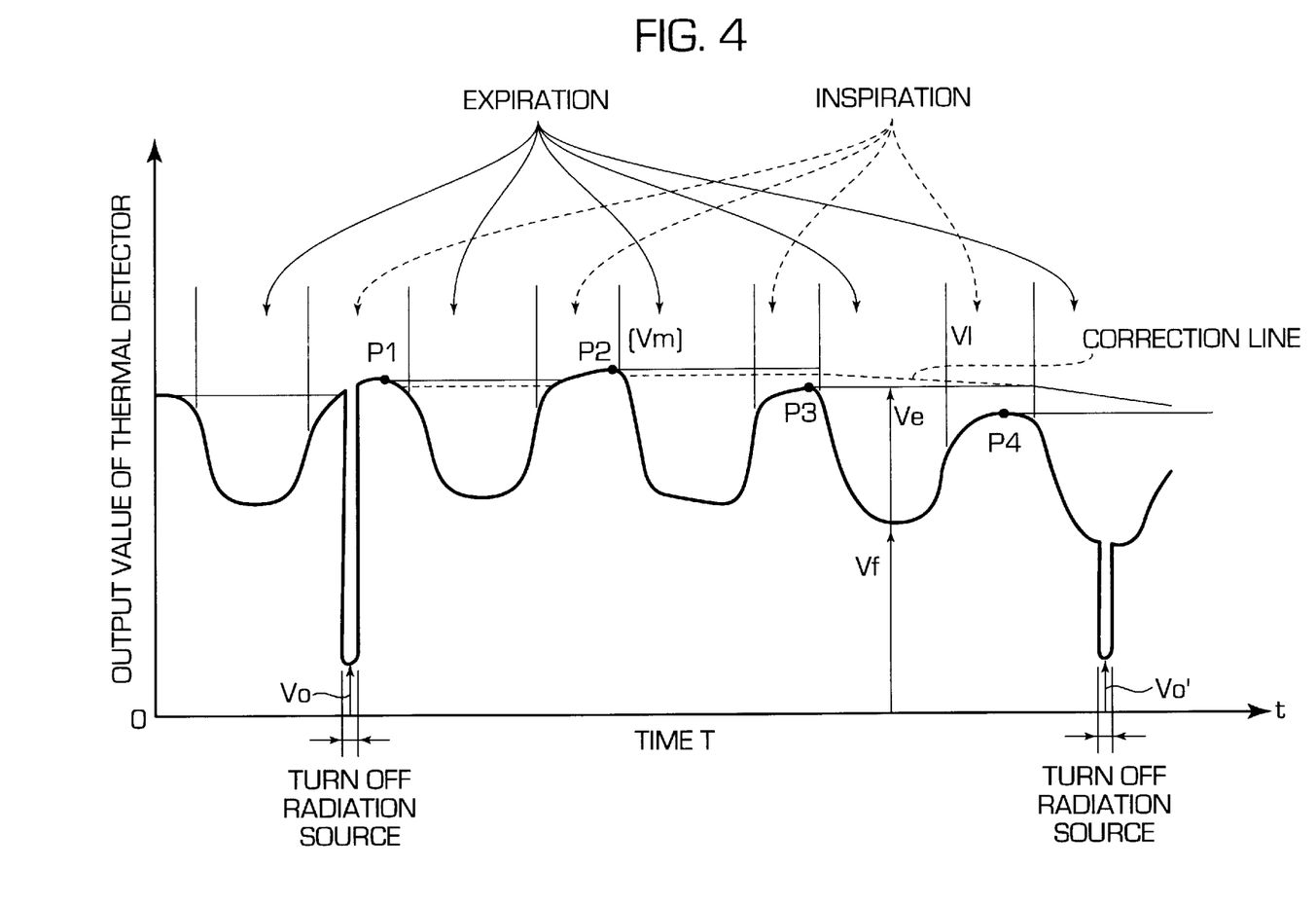
FIG. 4 is a diagram illustrating the operating theory of the invention by means of correction lines constructed by the Kalman filtering of the detection signal from the thermal detector.

FIG. 4 shows the waveforms of the corrected values that are delivered from a Kalman filter and on the basis of such corrected values, output from the thermopile is drift compensated in the second embodiment. Referring to FIG. 4, P1–P4 designate maxima that are detected from the thermopile during successive inspiration phases and Vm represents a maximum value for the inspiration phase that is picked up from the detected signal at point P2. As shown, Vm is on the solid line. On the other hand, the dashed line indicates a corrected value VI which is delivered as the best estimate from the Kalman filter and which can be computed by the following equation, with the maximum value Vm being entered as an input parameter:

$$VI(n+1)=VI(n)+(Vm-VI(n))/B(n+1) \quad (1)$$

where the function $B(n+1)$ is expressed by:

$$B(n+1)=(1+\alpha\, B(n))$$

where $\alpha$ is a predetermined Kalman coefficient which affects the correcting characteristics of the filter; n is the sampling interval taking discrete values such as 0, 1, 2, . . . ; $VI(n+1)$ is the filter output at the present time; $VI(n)$ is the filter output at the preceding point of time; and Vm is a maximum value of the detected signal stored at the present time. The initial values of VI and B are $VI(0)=0$ and $B(1)=1$.

Thus, the corrected value VI $(n+1)$ can be obtained by substituting the present maximum value for the thermopile into equation (1). As shown by the dashed line in FIG. 4, the corrected value $VI(n+1)$ closely follows and approaches the maxima that are detected in successive inspiration phases for entry into the computer. Hence, by determining the difference between this corrected value and the detected signal from the thermopile, one can obtain a density signal corresponding to the $CO_2$ concentration to be measured.

Figure 5:
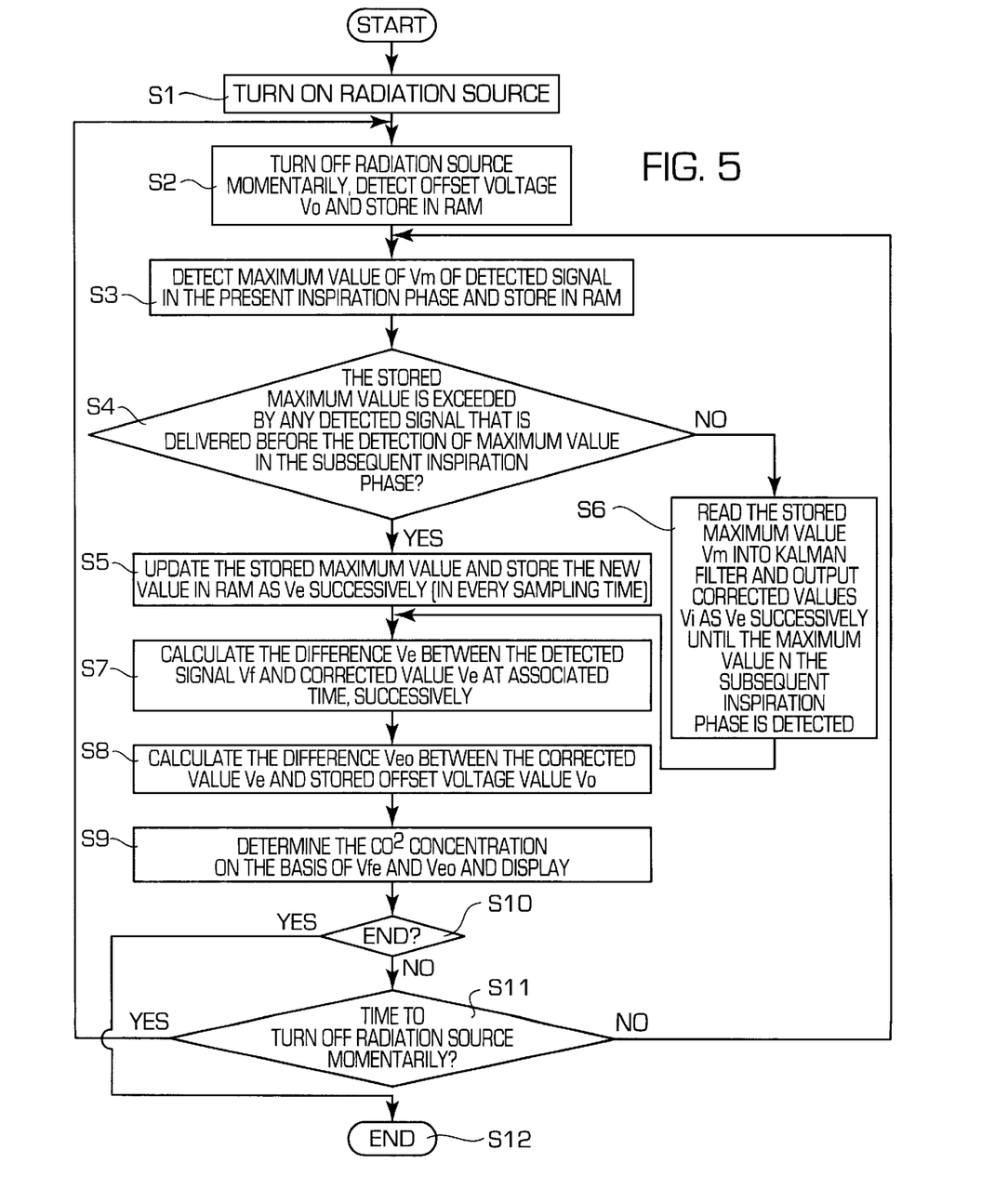
FIG. 5 is a flowchart describing the sequence of processing steps in the embodiment shown in FIG. 4.

The operation of the capnometer having this structure will now be described with reference to the flowchart shown in FIG. 5. At the commencement of measurement, the power switch (not shown) turns on the radiation source 1 (Step S1). Thereafter, the patient is allowed to breathe so that his respiratory gas goes into and comes out of the air way adapter T via the mouthpiece in his mouth.

The transmission of the radiation which varies with the change in the $CO_2$ concentration of the respiratory gas is received by the thermal detector 2 in such a way that the point at which the detector 2 delivers an increased output is recognized as an inspiration.

The radiation source 1 is turned off momentarily and then turned on by controlling switch SW, and when the radiation source is turned off, a minimum output value Vo is detected as the offset voltage value of thermopile and stored (Step S2).

During the inspiration phase, a maximum value Vm corresponding to $CO_2$ concentration of zero is picked up from the detection signal from the thermal detector 2 and stored in RAM 8 (Step S3). The desired maximum value can be identified by performing a suitable processing on the detection signal from the thermal detector 2, for example, by calculating the differential for successive data on the time base. It is determined whether the detected signal from the thermal detector 2 exceeds the maximum value stored in RAM 8, prior to the detection of a maximum value for the subsequent inspiration phase.

When the detected signal from the thermal detector 2 exceeds the maximum value stored in RAM 8, the latter is updated and the new value is stored in RAM 8 (Step S5). If the detected signal from the thermal detector 2 does not exceed the maximum value stored in RAM 8, the control unit 6 successively reads the stored maxima out of RAM 8 and performs Kalman filtering on the stored data in accordance with the above-described operating theory of the second embodiment of the invention, until a maximum value is detected in the subsequent inspiration phase, whereby corrected values Ve are successively delivered (Step S6).

Then, since a detected signal Vf from the thermal detector 2 is getting lower at a time subsequent to the detection of the present maximum value, the detected signal is recognized as representing an expiration phase. The difference Vfe between the detected signal Vf and the corrected value Ve, determined by Kalman filtering at the time when the detected signal Vf, is calculated (Step S7). This operation can be performed in real time. Further, the difference Veo between the corrected value Ve and the stored offset voltage value Vo is calculated (Step S8) and $CO_2$ concentration value is determined on the basis of the ratio of Vfe to Veo (Step S9).

As long as the measurement is not terminated (Step 10), the offset voltage value Vo is detected at the time when switch SW is turned off by switch control, stored and replaced (Step S11), and Step S2 through Step S9 are repeatedly performed. On the other hand, until switch SW is turned off by the switch control, Step S3 through Step S9 are continuously performed to measure the $CO_2$ concentration at each respiration.

The control unit 6 determines the $CO_2$ concentration on the basis of the ratio of Vfe to Veo, and obtains the $CO_2$ concentration changes as shown in FIG. 6. The determined concentration is displayed on the display unit 10. If the display unit is a bar graph, varying lengths of bars will appear in accordance with the $CO_2$ concentration changes as shown in FIG. 6.

Thus, corrected values are determined by Kalman filtering and drift compensation is accomplished by taking the difference between each corrected value and the associated detected signal. As a result, there is provided an apparatus capable of drift compensation in such a way that the compensated signal will not contain any point of discontinuity despite abrupt changed in the ambient temperature.

The reference value is calculated from the difference between the corrected value and the offset voltage value in the above-described embodiment. When the sensitivity is stable, it is possible to calculate the reference value from the difference between the maximum value and the offset voltage because under such circumstances, the corrected value is almost the same as the maximum value of the detection signal.

The radiation source 1 can be turned off at a period of unspecified intervals. If desired, period T at which the radiation source 1 is turned off may be predetermined. The period T may be preset and stored in ROM 9 or it may be set manually via the manipulating section 7. In either way, predetermining the period of turning off the radiation source 1 enables automatic detection of the detected signal from the thermal detector 2. This period may be set at any desired value such as 30 seconds or 1 minute depending on the ambient temperature. Alternatively, the radiation source 1 may be turned off at a period associated with the respiration, such as in synchronism with two or more respiration or when one breathing cycle (inspiration or expiration) ends. The number of respirations may be preset and stored in ROM 9 or it may be set manually via the manipulating section 7. If the radiation source 1 is turned off at a specified period, its turning off may sometimes coincide with the expiration phase and the data detected on this occasion is not useful. On the other hand, if the radiation source 1 is turned off in synchronism with the inspiration, the detected signal delivered during expiration phases can be corrected positively to insure consistency in $CO_2$ measurement.

A threshold value is set for the drift of the detected signal from the thermal detector 2 and the radiation source is turned off momentarily when the drift exceeds this specified value. For instance, two maximum values are picked up, one in the present inspiration phase and the other in the preceding inspiration phase, and if the difference between these values exceeds the threshold which is corresponding to the partial pressure 2 mmHg of $CO_2$, the radiation source 1 may be turned off, the period of turning off the radiation source may be shortened, or device may sound or display alarm to notify that the drift goes beyond the threshold. The threshold value may be set manually via the manipulating section 7 or, alternatively, it may be preliminary stored in ROM 9 such that the control unit 6 monitors it to control the turning off the radiation source 1. The provision of such threshold value for the drift of the detected signal from the thermal detector 2 ensures that the measurement of $CO_2$ concentration can be accomplished both positively and consistently even in environments where the ambient temperature varies greatly.

Another approach that can be taken is that a predetermined value is set for a change of the offset voltage value, which is detected when the radiation source is turned off, from the thermal detector 2 and when the change exceeds the threshold, the period of turning off the radiation source is shortened, or device sounds or displays alarm to notify that the drift goes beyond the threshold. About 2 mmhg is preferable as the predetermined threshold.

Thus, in the second embodiment of the invention, corrected values are determined by Kalman filtering and drift compensation is accomplished by taking the difference between each corrected value and the associated detection signal. As a result, there is provided a capnometer capable of drift compensation in such a way that the compensated signal will not contain any point of discontinuity despite abrupt changes in the ambient temperature.

Since both density signal and reference value are calculated using the corrected value in expiration phase which follow the change, both embodiments of the present invention provide more appropriate accurate measured concentration values, even if light intensity is reduced due to contamination of windows or sensitivity variations.

What is claimed is:

1. A capnometer comprising:
    a radiation source for irradiating infrared radiation to a respiratory gas;
    a thermal detector for sensing a transmission of said infrared radiation and for outputting a detection signal;
    means for turning said radiation source on and off at predetermined intervals;
    a memory for storing an output from said thermal detector;
    maximum value detecting means for detecting a maximum value of said detection signal output from said thermal detector for the present inspiration phase;
    minimum value detecting means for detecting a minimum output value, corresponding to an offset value, of said detection signal output from said thermal detector when said radiation source is turned off momentarily;
    corrected value determining means for determining a corrected value based upon said maximum value for the present inspiration phase,
    means for determining a density signal by calculating the difference between a subsequent detection signal, output from said thermal detector, and said corrected value;
    means for determining a reference value by calculating the difference between said corrected value and said minimum value for the present inspiration phase;
    means for determining the concentration of carbon dioxide by calculating a ratio of said density signal to said reference value.

2. The capnometer according to claim 1, wherein said corrected value determining means is arranged to calculate a straight line connecting the maximum value for the present inspiration phase and a second maximum value for a preceding inspiration phase and determining a correction line extending to a point of detection of a third maximum value during the next inspiration phase, and obtain the corrected value associated with said detection signal for the present phase.

3. The capnometer according to claim 1, wherein said corrected value determining means is arranged to subject said detection signal to predetermined filtering to output said corrected value.

4. The capnometer according to claim 1, wherein said corrected value determining means is arranged to subject said maximum values to Kalman filtering to output said corrected value.

5. The capnometer according to claim 1, wherein said corrected value determining means is arranged to update said maximum value to form an updated maximum value when said maximum value is exceeded by a value of said detection signal delivered from said thermal detector before the detection of a second maximum value during the subsequent inspiration phase, store the updated maximum value, read stored maximum values successively out of said memory, and to subject said stored maximum values to Kalman filtering to output a corrected value.

6. The capnometer to claim 1, wherein said means for turning said radiation source on and off turns off said radiation source at a predetermined cycle longer than a cycle of respiration.

7. The capnometer according to claim 1, wherein said means for turning said radiation source on and off turns off said radiation source in synchronism with inspiration.

8. The capnometer according to claim 1, wherein said means for turning said radiation source on and off turns off said radiation source when the difference between maximum values of said detection signal detected in adjacent inspiration phases exceeds a predetermined threshold.

9. The capnometer according to claim 1, wherein said means for turning said radiation source on and off is further arranged to reduce an off-time interval of said radiation source when the difference between maximum values of said detection signal detected in adjacent inspiration phases exceeds a predetermined threshold.

10. The capnometer according to claim 1, further comprising:
    alarm means for notifying an operator when the difference between maximum values of said detection signal detected in adjacent inspiration phases exceeds a predetermined threshold.

11. The capnometer according to claim 1, further comprising:
    means for comparing said offset voltage value for the present phase and preceding phases.

12. The capnometer according to claim 11, wherein said means for comparing is arranged to control a period of turning off said radiation source to reduce said off-time interval of said radiation source when changes of said maximum values of said detection signal detected in adjacent inspiration phases exceeds a predetermined threshold.

13. The capnometer according to claim 11, further comprising:
   means for notifying an operator when changes of said maximum values of said detection signal detected in adjacent inspiration phases exceeds a predetermined threshold.

14. A capnometer comprising:
   a radiation source for irradiating infrared radiation to a respiratory gas;
   a thermal detector for sensing the transmission of said infrared radiation and for outputting a detection signal;
   a memory for storing an output from said thermal detector;
   maximum value detecting means for detecting a maximum value of said detection signal output from said thermal detector for the present inspiration phase;
   corrected value determining means for determining a corrected value based upon said maximum value for the present inspiration phase;
   means for determining a density signal by calculating the difference between a subsequent detection signal, output from said thermal detector, and said corrected value;
   means for determining the concentration of carbon dioxide on the basis of said density signal.

15. The capnometer according to claim 14, wherein said corrected value determining means is arranged to calculate a straight line connecting the maximum value for the present inspiration phases, and a second maximum value for the preceding inspiration phase and determining a correction line extending to a potential point of detection of a third maximum value during the next inspiration phase, and obtain the corrected value associated with said detection signal for the present inspiration phase.

16. The capnometer according to claim 14, wherein said corrected value determining means is arranged to subject said detection signal to predetermined filtering to output a corrected value.

17. The capnometer according to claim 14, wherein said corrected value determining means is arranged to subject said maximum values to Kalman filtering to output said corrected value.

18. The capnometer according to claim 14, wherein said corrected value determining means is arranged to update said maximum value to form an updated maximum value when said maximum value is exceeded by a value of said detection signal delivered from said thermal detector before the detection of a second maximum value during the subsequent inspiration phase, store the updated maximum value, read stored maximum values successively out of said memory, and to subject said stored maximum values to Kalman filtering to output a corrected value.

* * * * *